US012746213B2

(12) United States Patent
Roussis et al.

(10) Patent No.: US 12,746,213 B2
(45) Date of Patent: Sep. 29, 2026

(54) PHARMACEUTICAL FORMULATION COMPRISING POLYMERIC MICRO-/NANOFIBERS INCORPORATING ECHINOCHROME A

(71) Applicant: NATIONAL AND KAPODISTRIAN UNIVERSITY OF ATHENS, Athens (GR)

(72) Inventors: Vasileios Roussis, Athens (GR); Efstathia Ioannou, Athens (GR); Stefanos Kikionis, Athens (GR); Georgia Valsami, Athens (GR); Panagiotis Mavrogiorgis, Athens (GR); Paraskevi Papakyriakopoulou, Athens (GR)

(73) Assignee: NATIONAL AND KAPODISTRIAN UNIVERSITY OF ATHENS, Athens (GR)

( * ) Notice: Subject to any disclaimer, the term of this patent is extended or adjusted under 35 U.S.C. 154(b) by 0 days.

(21) Appl. No.: 19/128,313

(22) PCT Filed: Nov. 13, 2023

(86) PCT No.: PCT/EP2023/081546
§ 371 (c)(1),
(2) Date: May 8, 2025

(87) PCT Pub. No.: WO2024/120750
PCT Pub. Date: Jun. 13, 2024

(65) Prior Publication Data

US 2026/0007616 A1 Jan. 8, 2026

(30) Foreign Application Priority Data

Dec. 7, 2022 (GR) .............................. 20220101012

(51) Int. Cl.
*A61K 9/70* (2006.01)
*A61K 47/32* (2006.01)
*A61K 47/34* (2017.01)
*A61K 47/36* (2006.01)
*A61K 47/38* (2006.01)
*A61K 47/42* (2017.01)

(52) U.S. Cl.
CPC ................ *A61K 9/70* (2013.01); *A61K 47/32* (2013.01); *A61K 47/34* (2013.01); *A61K 47/36* (2013.01); *A61K 47/38* (2013.01); *A61K 47/42* (2013.01)

(58) Field of Classification Search
None
See application file for complete search history.

(56) References Cited

PUBLICATIONS

Vasileva et al. (Development of new drug froms based on echinochrome a using electrospun micro/nanofibers; Vestnik FEB RAS 2018 No. 8 Supplement). (Year: 2018).*
International Search Report issued in corresponding International Application No. PCT/EP2023/081546, dated Mar. 26, 2024, pp. 1-2.
Written Opinion of the International Searching Authority issued in corresponding International Application No. PCT/EP2023/081546, dated Mar. 26, 2024, pp. 1-4.
Vasileva, E. A. et al., "Development of new drug forms based on echinochrome a using electrospun micro/nanofibers" Vestnike FEB RAS (2018) pp. 169-170, No. 6, XP002810990.

* cited by examiner

*Primary Examiner* — Melissa S Mercier
(74) *Attorney, Agent, or Firm* — Carter, DeLuca & Farrell LLP; George Likourezos

(57) ABSTRACT

The invention relates to the development of a new pharmaceutical formulation for use as a medicament, in particular in anti-inflammatory diseases, and comprises of polymeric micro-/nanofibers incorporating echinochrome A. The composition provides increased stability and solubility, as well as controlled release for echinochrome A, while offering the potential for its targeted delivery.

9 Claims, 9 Drawing Sheets

PHARMACEUTICAL FORMULATION COMPRISING POLYMERIC MICRO-/NANOFIBERS INCORPORATING ECHINOCHROME A

CROSS-REFERENCE TO RELATED APPLICATION(S)

This application is a national stage application filed under 37 U.S.C. 371 based on International Patent Application No. PCT/EP2023/081546, filed Nov. 13, 2023, which claims the benefit of and priority to Greece Patent Application Serial No. 20220101012 filed on Dec. 7, 2022, the entire contents of each of which are incorporated herein by reference in their entirety.

FIELD OF THE INVENTION

The invention relates to the field of pharmacy, namely to the development of a new pharmaceutical formulation of echinochrome A for use as a medicament; in particular, it concerns a composition comprising polymeric micro-/nanofibers incorporating echinochrome A, providing increased stability and solubility, as well as controlled release for echinochrome A, while offering the potential for its targeted delivery.

BACKGROUND OF THE INVENTION

Echinochrome A is a marine-derived naphthoquinone (7-ethyl-2,3,5,6,8-pentahydroxy-1,4-naphthoquinone) and is the most common pigment found in various sea urchin species [1]. It is isolated as a red crystalline powder and in the form of its sodium salts represents the active ingredient of the clinically available drug Histochrome® (Russian Federation registration number P N 002362/01-2003) which has been developed at the G.B. Elyakov Pacific Institute of Bioorganic Chemistry, Far-Eastern Branch of the Russian Academy of Science (Vladivostok, Russia) [2]. Histochrome® is used as a cardioprotective and antioxidant drug for the treatment of various cardiovascular diseases, such as coronary heart disease, and for reducing the necrosis zone in myocardial infarction (Russian Federation registration number P N 002363/01-2003) [3]. Histochrome® is also used in ophthalmology for the treatment of a variety of ocular diseases, such as macular degeneration, cornea and retina degenerative diseases, primary open-angle glaucoma, post-traumatic hemorrhages, diabetic retinopathy, and dyscirculatory disorders in the central artery and vein of the retina (Russian Federation registration number P N 002363/02-2003) [4].

Echinochrome A simultaneously blocks a number of free radical reactions: it neutralizes reactive oxygen species, nitric oxide and peroxide radicals, it chelates metal ions, it inhibits lipid peroxidation, and it regulates the levels of antioxidant enzymes. Over the last several years, there has been an increasing interest for the commercial application of echinochrome A, since, besides possessing antioxidant activity, it has been reported to exhibit anti-inflammatory [5], antiviral [6], and antibacterial [7] activities, among others [8].

Currently, echinochrome A is used only in the form of an isotonic solution of its di- and tri-sodium salts for injection. The poor solubility of echinochrome A in water, in combination with its sensitivity to oxidation leading to low stability of its solutions, severely restrict its use in the pharmaceutical industry, prohibiting up to now its oral, buccal, nasal or transdermal administration.

Recent attempts to increase the solubility and effectiveness of echinochrome A include the development of (i) derivatives of polyethylene glycol encapsulating echinochrome A, exhibiting improved water solubility and formation of stable solutions [9], (ii) a water-soluble complex of beta-cyclodextrin-histochrome, showing prolonged antioxidant activity [10], (iii) carrageenan gel beads as a release delivery system of echinochrome A [11], (iv) carrageenan-echinochrome A complexes, exhibiting increased stability/solubility in aqueous media and significant gastroprotective activity [12], (v) liposomes based on egg lecithin/cholesterol and the carrageenan-echinochrome A complex, possessing mucoadhesive properties [13], (vi) echinochrome A complexes with ascorbic acid and α-tocopherol, exhibiting antioxidant and antiviral effects [14] and (vii) echinochrome A incorporated in micro-/nanofibers composed of a single commercially used in pharmaceutical technology polymer [15].

Among these prior art formulations, the most relevant for oral administration of echinochrome A is the preparation of a water-soluble complex of carrageenan-echinochrome A in a weight ratio of 5:1, exhibiting prolonged gastroprotective, cardioprotective and antioxidant activity [16].

The inclusion of echinochrome A in carrageenan matrices increased its stability and solubility in an aqueous medium and it was shown that echinochrome A was released from the complexes 10-20% slower than from an aqueous solution, offering a slightly prolonged action.

The disadvantages of this prototypic pharmaceutical form of echinochrome A for oral administration are its short-term stability (60 hours), its uncontrolled release and the lack of possibility for targeted delivery.

In addition, incorporation of echinochrome A in single-polymer micro-/nanofibers could provide prolonged release of echinochrome A at pH 6.8 when polycaprolactone, hypromellose or polyethylene oxide is used [15].

However, the disadvantages of this prototypic pharmaceutical form of echinochrome A are its uncontrolled release, the lack of possibility for targeted delivery and its undetermined stability.

DESCRIPTION OF THE INVENTION

The present invention discloses a pharmaceutical form comprising of micro-/nanofibers of various polymers incorporating echinochrome A for use as a medicament.

The objective of the present invention is to expand the range of applications of echinochrome A by developing a novel and highly effective pharmaceutical formulation suitable for oral administration offering targeted delivery and controlled release of echinochrome A, which can be used as a medicament for the prevention/treatment of health problems. In a preferred embodiment of the use of the said pharmaceutical formulation, it includes the treatment of inflammatory diseases. In a further embodiment the therapeutic use of the pharmaceutical formulation includes the following health problems that echinochrome A can treat:

as a cardioprotective and antioxidant drug for the prevention/treatment of various cardiovascular diseases, eg. coronary heart disease, ischemic heart disease, ischemic or hemorrhagic stroke (in vivo, currently used as a drug in the form of isotonic solution)

in ophthalmology for the treatment of a variety of ocular diseases, including macular degeneration, cornea and retina degenerative diseases, primary open-angle glaucoma, post-traumatic hemorrhages, diabetic retinopathy, and dyscirculatory disorders in the central artery and vein of the retina (in vivo, currently used as a drug in the form of isotonic solution)

as an anti-inflammatory and gastroprotective agent, against inflammatory diseases of the gastrointestinal tract, colitis and inflammatory bowel diseases (the treatment has been tested in vivo)

as an antioxidant and hypoglycemic agent, for the treatment of diabetes (the treatment has been tested in vivo)

as an antiviral agent, against viruses including tick-borne encephalitis virus and herpes simplex viruses of types 1 and 2 (the treatment has been tested in vivo)

as an antibacterial agent, for the suppression of the bacterial activity in renal injury (the treatment has been tested in vitro)

for the treatment of chronic inflammatory skin diseases, including atopic dermatitis (the treatment has been tested in vivo)

for the treatment of neurodegenerative diseases, including Alzheimer's disease (the treatment has been tested in vitro)

as an anticancer agent, including against Ehrlich ascites carcinoma, as an adjuvant treatment for chemotherapy (the treatment has been tested in vivo).

The pharmaceutical formulation of the present invention comprising of micro-/nanofibers composed of various polymers incorporating echinochrome A, offers increased stability and solubility, controlled release and the potential for targeted delivery.

Micro/nanofibrous matrices composed of one or more biocompatible polymers (e.g., polyvinylpyrrolidone, polycaprolactone, polyethylene oxide, cellulose acetate, methyloxypropylcellulose, alginate, chitosan), selected on the basis of their physicochemical properties (e.g., solubility, biodegradability, pH sensitivity) in relation to the desired route of administration (e.g., oral, buccal, nasal, transdermal) and the desired therapeutic scheme (e.g., release profile, dosage, targeted delivery) incorporating echinochrome A in appropriate concentrations for optimal efficacy according to the desired application has been prepared by various methods (e.g., electrospinning, centrifugal spinning, meltblowing, self-assembly, phase separation and extrusion) and tested.

The selection of the polymers used as carriers of echinochrome A can affect the architecture of the micro-/nanofibrous matrices, and in turn the encapsulation efficiency and the release profile, thus allowing for the preparation of micro-/nanofibrous patches according to the desired specifications/properties for different routes of administration and different therapeutic targets, offering the potential for targeted delivery. For example, when echinochrome A should be released in the stomach (pH<2.0), polymers soluble in acidic pH would be selected and blended with polymers of variable solubility in order to achieve different release profiles (e.g., burst effect could be achieved with the use of another hydrophilic polymer or prolonged release could be achieved with the use of a slightly water-soluble polymer). In contrast, when echinochrome A should be released in the duodenum (pH around 6.0) or in the rest of the small intestine (pH between 6 to 7 in the jejunum, to about 7.5 in the ileum) or colon (pH around 8.0), polymers not soluble in acidic pH but soluble in neutral to slightly basic pH would be selected and blended with polymers of variable solubility in order to achieve prolonged release profiles.

In a preferred embodiment the invention discloses a pharmaceutical composition for use as a medicament, comprising two or more biocompatible polymers or one or more diblock copolymer and echinochrome A characterized in that echinochrome A is incorporated in fibers of the biocompatible polymers or the diblock copolymer and that the said biocompatible polymers or the blocks of the said copolymer have different hydrophilicity and pH sensitivity so that the pharmaceutical composition provides controlled release and/or targeted delivery of echinochrome A in different pH environments.

In another preferred embodiment, the pharmaceutical composition for use as a medicament comprises of two or more biocompatible polymers which are natural and preferably alginate, chitosan, gelatin, hyaluronic acid, silk fibroin, glycosaminoglycans, ulvan, carrageenan, fucoidan, synthetic and preferably polyvinylpyrrolidone, polycaprolactone, polyethylene oxide, cellulose acetate, methyloxypropylcellulose, polylactic acid, polyhydroxybutyrate, polyglycolic acid, polyethylene glycol, polyacrylic acid, polyurethane, eudragit or a combination of natural and synthetic polymers thereof.

Another aspect of the invention relates to the fabrication of the micro-/nanofibers of the pharmaceutical composition. In an embodiment they are fabricated through electrospinning or centrifugal spinning or meltblowing or self-assembly or phase separation and extrusion of echinochrome A dissolved or dispersed in the said biocompatible polymers.

It was found advantageous when the micro-/nanofibers are fabricated through electrospinning of a solution of echinochrome A dissolved or dispersed in the said biocompatible polymers in a concentration between 1 and 50% w/w.

In another embodiment of the pharmaceutical composition for use as a medicament, the said biocompatible polymers are blended in one spinning solution that is electrospun as is or are used to form independent spinning solutions that are simultaneously electrospun using a parallel or antiparallel setup to fabricate a composite non-woven.

The said pharmaceutical composition for therapeutic use is prepared in solid form or liquid suspension, in a pharmaceutically acceptable diluent. These preparations can be administered via any appropriate route of administration. In a preferred embodiment, the route of administration of the pharmaceutical composition for therapeutic use is oral, or topical or transdermal or buccal or nasal or rectal or parenteral (including subcutaneous, intraperitoneal, intradermal, intramuscular, intravenous) or a combination thereof.

DETAILED DESCRIPTION AND EXAMPLES

Figure 1A:
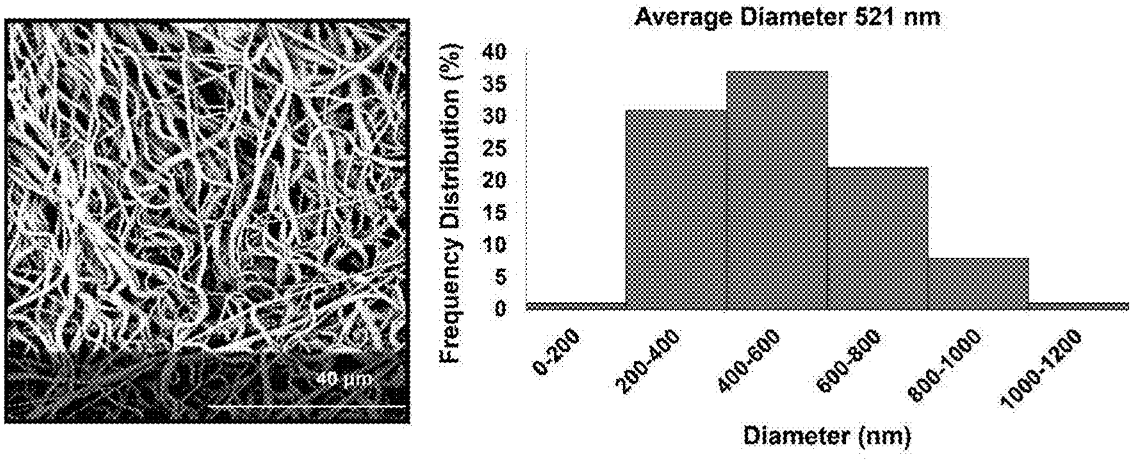
FIG. 1. SEM images and diameter distribution histograms of (a) PCL-EchA, (b) PVP-EchA, (c) PCL-EchA/PVP-EchA (1:3), (d) PCL-EchA/PVP-EchA (1:1), (e) PCL-EchA/PVP-EchA (3:1) and (f) [PCL-PVP(1:3)]-EchA fibers.
Figure 1B:
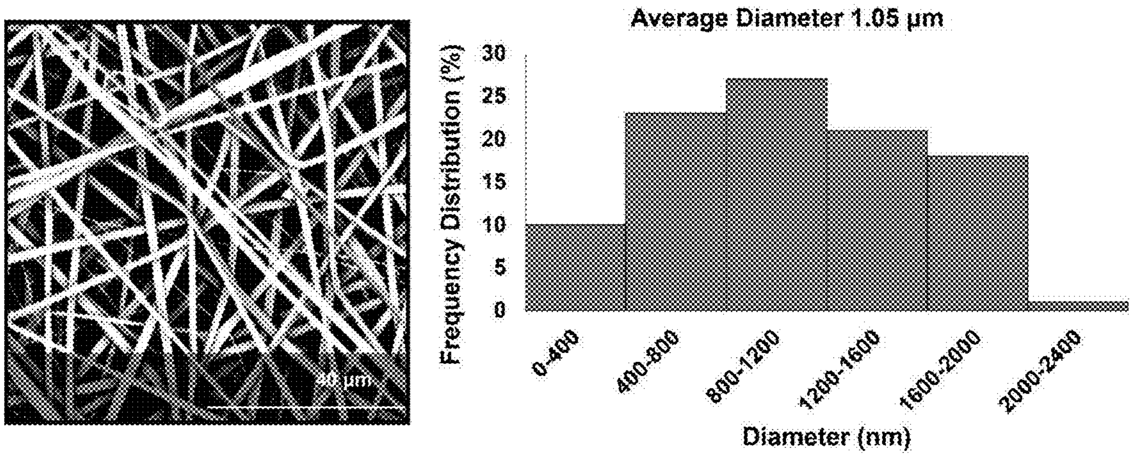
Figure 1C:
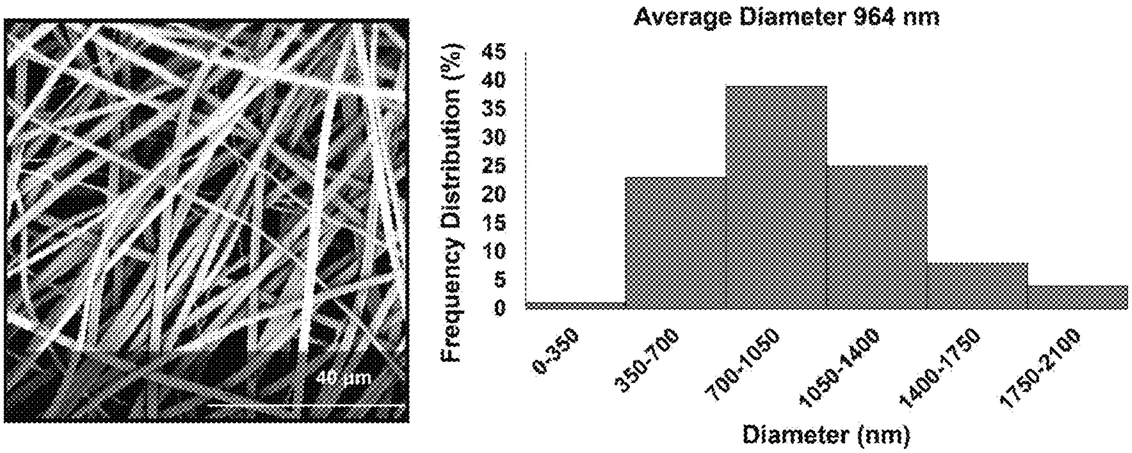
Figure 1D:
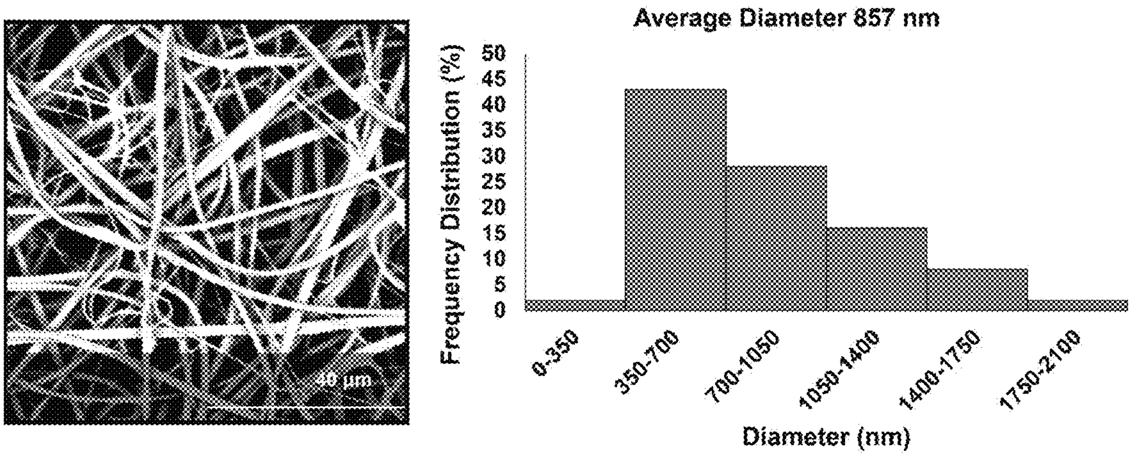
Figure 1E:
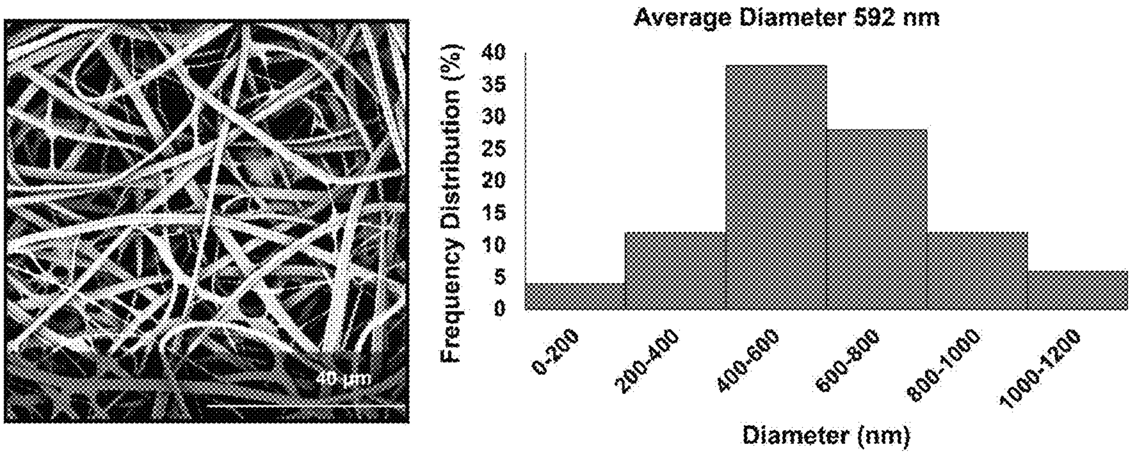
Figure 1F:
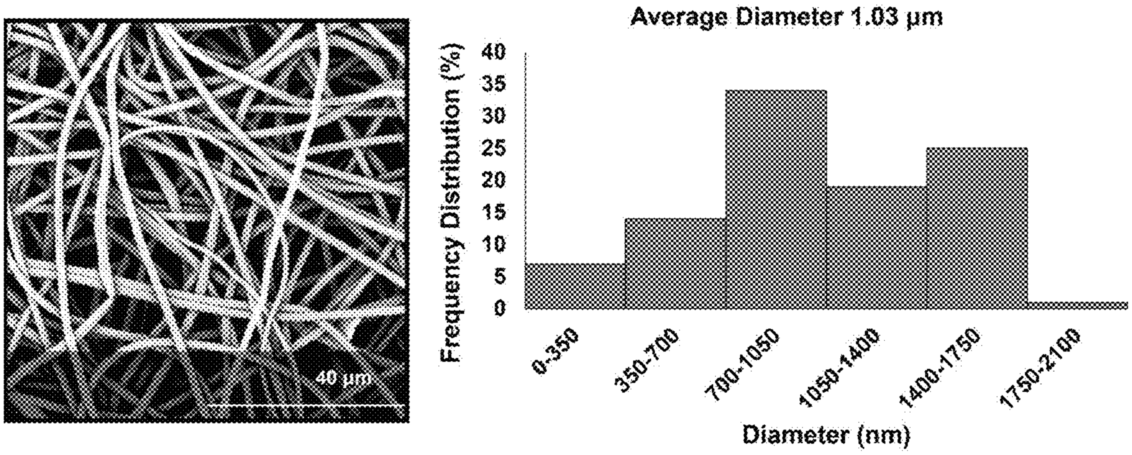

A method for obtaining the claimed micro-/nanofibers incorporating echinochrome A, the study of their physicochemical properties and their release into biological media for controlled release oral administration are described in detail in the following examples. In one example, the technique of electrospinning was used for the preparation of the micro-/nanofibers incorporating echinochrome A since it is an efficient, versatile, simple, cost-effective and up-scalable method for the production of polymeric fibers with diameters ranging from submicron down to the nanometer scale, offering the possibility to produce fibers with tailor-made properties and diverse morphologies by changing a wide range of parameters (e.g., applied voltage, polymer flow rate, tip-to-collector distance). To demonstrate the potential of the invention for controlled release and targeted delivery, the hydrophobic polycaprolactone (PCL) and the hydrophilic polyvinylpyrrolidone (PVP) were selected as example polymers either alone or blended in various ratios, resulting in the preparation of micro-/nanofibers exhibiting different release profiles.

Specifically, micro/nanofibers composed of PCL or/and PVP in various combinations loaded with echinochrome A (EchA) were fabricated using the technique of electrospinning. Electrospinning was conducted using a γ-High Voltage Research DC power supply generator of 50 kV maximum voltage (Gamma High Voltage Research) with the spinning solutions being loaded into 10 mL disposable syringes fitted with stainless steel blunt needles (23 G). The syringes were mounted on a horizontally positioned programmable syringe pump (Harvard PHD 2000, Harvard Apparatus) and the produced nanofibers were deposited on aluminum foil wrapped on a RC-6000 (NaBond Technologies) rotating drum collector at a rotation speed of 500 rpm. Temperature and relative humidity were 21±2° C. and 60±5%, respectively. All spinning solutions were prepared by dissolving the appropriate polymers and echinochrome A at various organic solvent systems at room temperature under stirring for 24 h to ensure their homogeneity. Echinochrome A was added to each polymer solution to afford a 10% w/w (weight to matrix weight) total concentration of echinochrome A. Once formed, the non-woven micro-/nanofibers were removed from the surface of the collector in dry state.

Detailed Examples (i) preparation of micro-/nanofibers of PCL incorporating echinochrome A (PCL-EchA): PCL (molecular weight 80,000) was dissolved at a concentration of 12% w/v in a mixture of dichloromethane:dimethylformamide (8:2 v/v) (for example, 1.2 g of PCL in 10 mL of the solvent). Subsequently. EchA was added to the polymer solution at a concentration of 1.333% w/v (for example, 0.133 g of EchA per 10 mL of a 12% w/v PCL solution). The solution of PCL with EchA was loaded into a disposable syringe and electrospinning was carried out with the solution feeding rate fixed at 3 mL/h, applied voltage fixed at 25 kV and tip-to-collector distance fixed at 15 cm.

(ii) preparation of micro-/nanofibers of PVP incorporating echinochrome A (PVP-EchA): PVP (molecular weight 1,300,000) was dissolved at a concentration of 12% w/v in ethanol (for example, 1.2 g of PVP in 10 mL of the solvent). Subsequently, EchA was added to the polymer solution at a concentration of 1.333% w/v (for example, 0.133 g of EchA per 10 mL of a 12% w/v PVP solution). The solution of PVP with EchA was loaded into a disposable syringe and electrospinning was carried out with the solution feeding rate fixed at 3 mL/h, applied voltage fixed at 25 kV and tip-to-collector distance fixed at 15 cm.

(iii) preparation of blended micro-/nanofibers of PCL and PVP in a ratio of 1:3 incorporating echinochrome A (PCL-EchA/PVP-EchA (1:3)): To obtain blended micro-/nanofibers of PCL and PVP in a 1:3 ratio incorporating EchA, the solutions of PCL and PVP were prepared separately, as described above (in examples i and ii) and EchA was added to each polymer solution at a concentration of 1.333% w/v. The PCL-EchA and PVP-EchA spinning solutions were co-electrospun on an antiparallel setup to ensure the homogeneous blending of the PCL and PVP polymer fibers. Electrospinning was performed with the applied voltage and tip-to-collector distance fixed at 25 kV and 15 cm, respectively, with the syringes mounted on two horizontally opposed programmable syringe pumps. The feeding rate of the PCL-EchA spinning solution was adjusted to 1.5 mL/h, whereas the feeding rate of the PVP-EchA spinning solution was fixed at 4.5 mL/h.

(iv) preparation of blended micro-/nanofibers of PCL and PVP in a ratio of 1:1 incorporating echinochrome A (PCL-EchA/PVP-EchA (1:1)): To obtain blended micro-/nanofibers of PCL and PVP in a 1:1 ratio incorporating EchA, the solutions of PCL and PVP were prepared separately, as described above (in examples i and ii) and EchA was added to each polymer solution at a concentration of 1.333% w/v. The PCL-EchA and PVP-EchA spinning solutions were co-electrospun on an antiparallel setup to ensure the homogeneous blending of the PCL and PVP polymer fibers. Electrospinning was performed with the applied voltage and tip-to-collector distance fixed at 25 kV and 15 cm, respectively, with the syringes mounted on two horizontally opposed programmable syringe pumps. The feeding rates of the PCL-EchA and PVP-EchA spinning solutions were adjusted to 3 mL/h.

(v) preparation of blended micro-/nanofibers of PCL and PVP in a ratio of 3:1 incorporating echinochrome A (PCL-EchA/PVP-EchA (3:1)): To obtain blended micro-/nanofibers of PCL and PVP in a 3:1 ratio incorporating EchA, the solutions of PCL and PVP were prepared separately, as described above (in examples i and ii) and EchA was added to each polymer solution at a concentration of 1.333% w/v. The PCL-EchA and PVP-EchA spinning solutions were co-electrospun on an antiparallel setup to ensure the homogeneous blending of the PCL and PVP polymer fibers. Electrospinning was performed with the applied voltage and tip-to-collector distance fixed at 25 kV and 15 cm, respectively, with the syringes mounted on two horizontally opposed programmable syringe pumps. The feeding rate of the PCL-EchA spinning solution was adjusted to 4.5 mL/h, whereas the feeding rate of the PVP-EchA spinning solution was fixed at 1.5 mL/h.

(vi) preparation of composite micro-/nanofibers of PCL and PVP in a ratio of 1:3 incorporating echinochrome A ([PCL-PVP(1:3)]-EchA): To obtain composite micro-/nanofibers of PCL and PVP in a 1:3 ratio incorporating EchA, PCL at a concentration of 3% w/v and PVP at a concentration of 9% w/v were dissolved in a mixture of dichloromethane:ethanol (7:3 v/v) (for example, 0.3 g of PCL and 0.9 g of PVP in 10 mL of the solvent). Subsequently, EchA was added to the polymer solution at a concentration of 1.333% w/v (for example, 0.133 g of EchA per 10 mL of the solvent). The solution of PCL/PVP with EchA was loaded into a disposable syringe and electrospinning was carried out with the solution feeding rate fixed at 3 mL/h, applied voltage fixed at 25 kV and tip-to-collector distance fixed at 15 cm.

The chemical integrity of echinochrome A after electrospinning was verified by $^1$H NMR and UV/Vis spectroscopic analyses of the recovered compound following extraction of echinochrome A from the fabricated fiber mats. Echinochrome A remains stable during electrospinning and is completely incorporated into micro-/nanofibers (more than 95% of the load).

The morphological characterization of the micro-/nanofibers (FIG. 1) was performed using a PhenomWorid (Thermo Fischer Scientific) desktop scanning electron microscope (SEM) with tungsten filament (10 kV) and a charge reduction sample holder. It was shown that micro-/nanofibers of cylindrical shape were successfully obtained from all spinning solutions. The range of diameters and the average diameters of the produced micro-/nanofibers are shown in Table 1.

TABLE 1

Range of diameter and average diameter of the produced micro-/nanofibers.

| Micro-/nanofibers | Range of diameter | Average diameter |
|---|---|---|
| PCL-EchA | 185 nm-1.15 μm | 521 ± 96 nm |
| PVP-EchA | 24 nm-2.28 μm | 1.05 ± 0.16 μm |
| PCL-EchA/PVP-EchA (1:3) | 77 nm-1.92 μm | 964 ± 183 nm |
| PCL-EchA/PVP-EchA (1:1) | 105 nm-1.92 μm | 857 ± 150 nm |
| PCL-EchA/PVP-EchA (3:1) | 34 nm-1.16 μm | 592 ± 115 nm |
| [PCL-PVP(1:3)]-EchA | 78 nm-1.87 μm | 1.03 ± 0.16 μm |

Figure 2A:
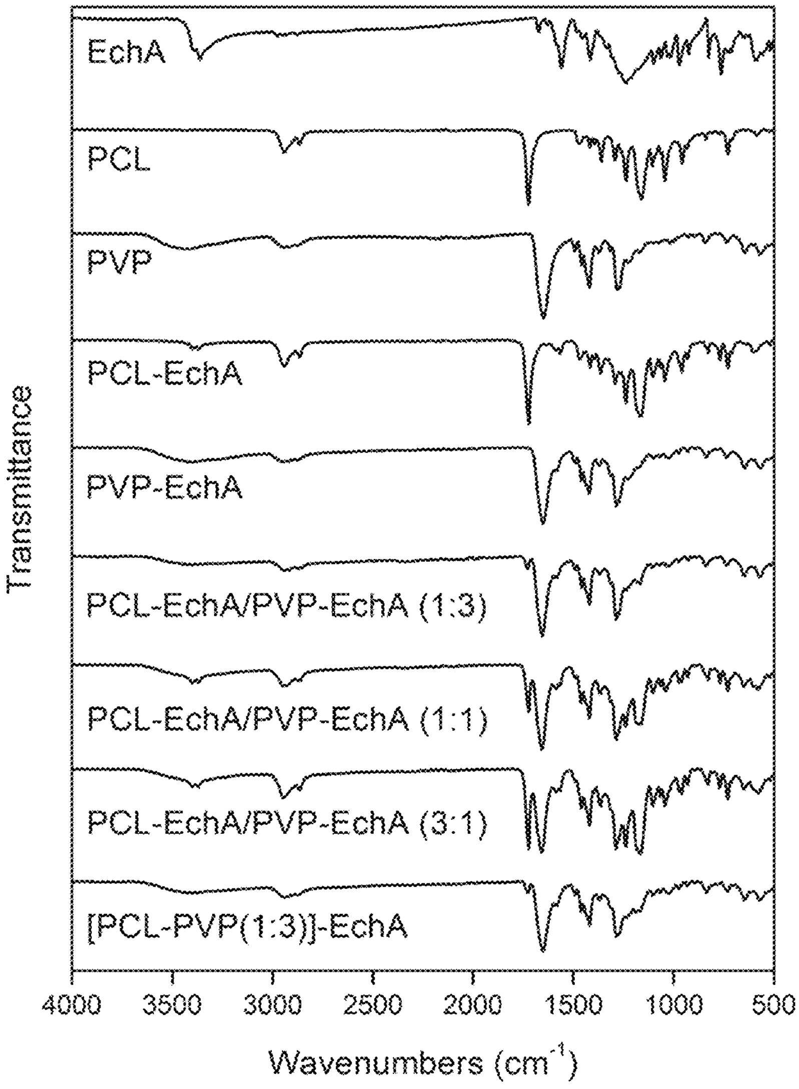
FIG. 2. (a) FTIR spectra, (b) TGA and (c) DSC thermograms of EchA, PCL, PVP, PCL-EchA, PVP-EchA, PCL-EchA/PVP-EchA (1:3), PCL-EchA/PVP-EchA (1:1), PCL-EchA/PVP-EchA (3:1) and [PCL-PVP(1:3)]-EchA fibrous matrices.

The FTIR spectra of the fabricated fibers, recorded using the attenuated total reflection (ATR) method on an FTIR Bruker Alpha II spectrometer, revealed the characteristic signals of their ingredients (FIG. 2*a*). Due to the high amount of PCL and PVP dominating the fibers, all fibrous matrices exhibited mainly the characteristic absorption bands of the polymeric components. The incorporation of the echinochrome A into the polymeric fibers was evident by the absorption band at 1560 cm$^{-1}$ attributed to carbonyl —C═O stretching vibration as its other characteristic signals were overlapping with those of PCL and/or PVP.

Figure 2B:
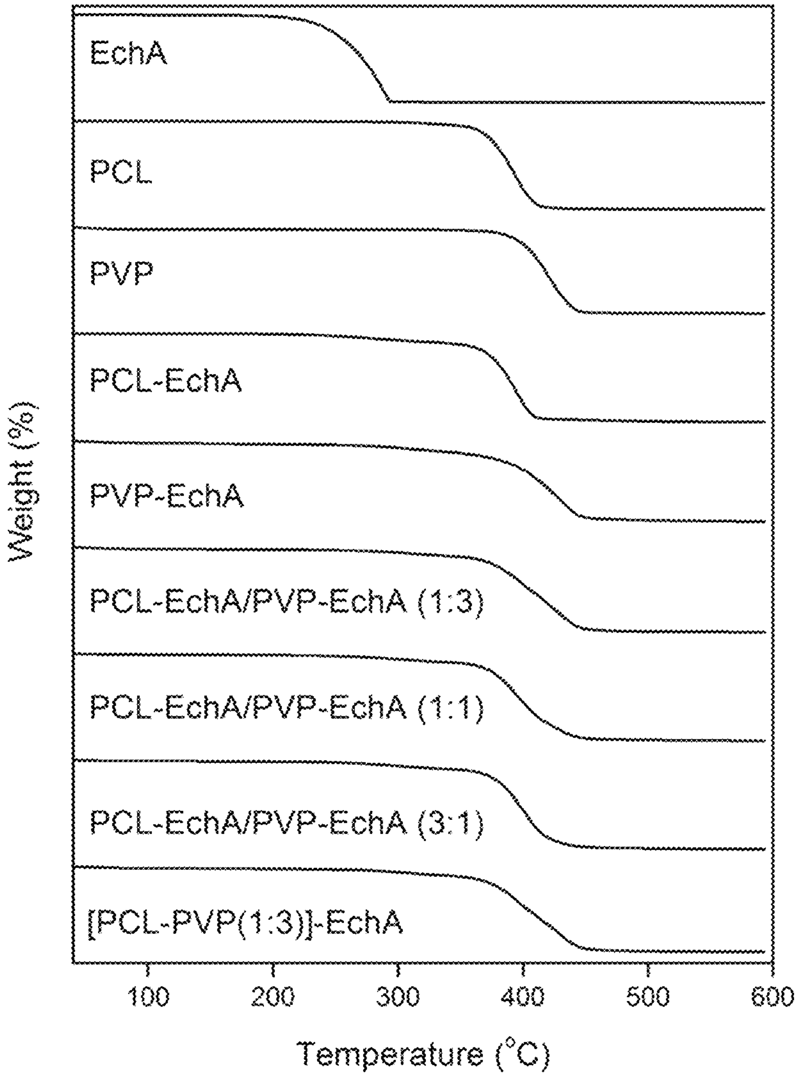
Figure 2C:
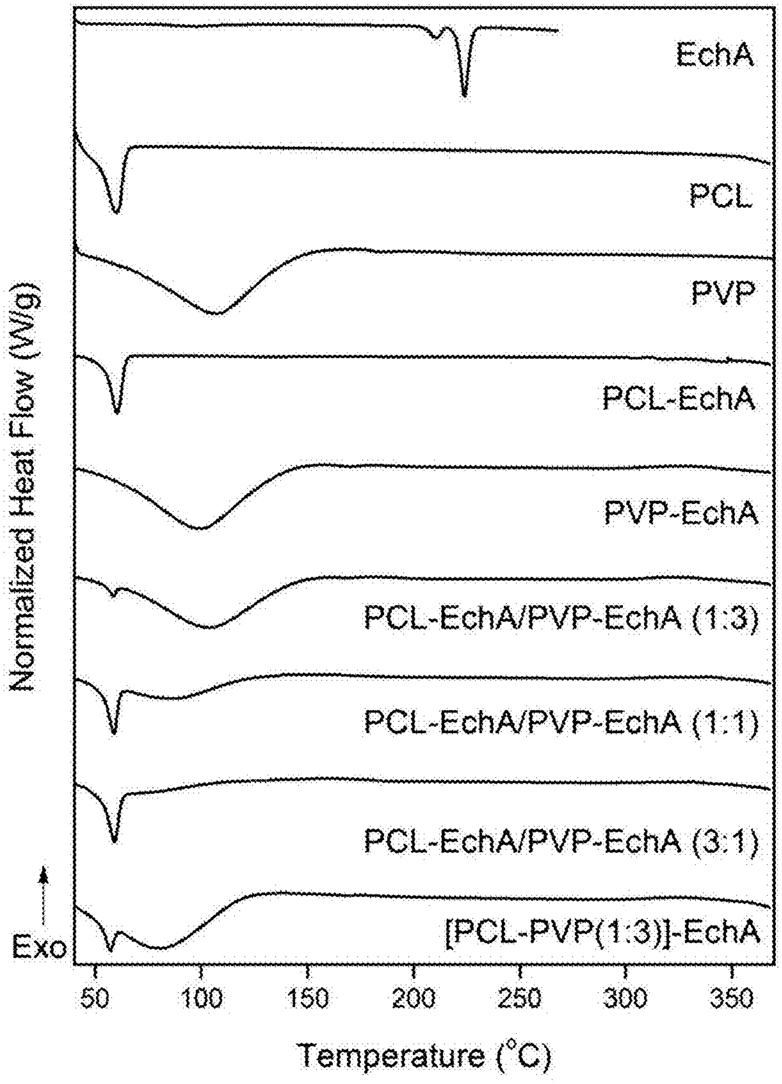

The fabricated micro-/nanofibers, as well as the utilized raw materials, were physicochemically characterized by TGA and DSC analyses (FIGS. 2*b* and 2*c*), using a TA Thermogravimetric Analyzer (TGA 55, TA Instruments) and a TA Thermal Analyzer (Discovery DSC 25, TA instruments), respectively. The thermogravimetric curves of the designed matrices revealed the synergistic degradation phenomena of the combined ingredients. Worth-noting is that none of the characteristic thermal events of EchA were evident in the thermograms of the micro-/nanofibers indicating the absence of crystalline EchA within the fabricated fibers, most probably due to its conversion to the amorphous form.

Figure 3A:
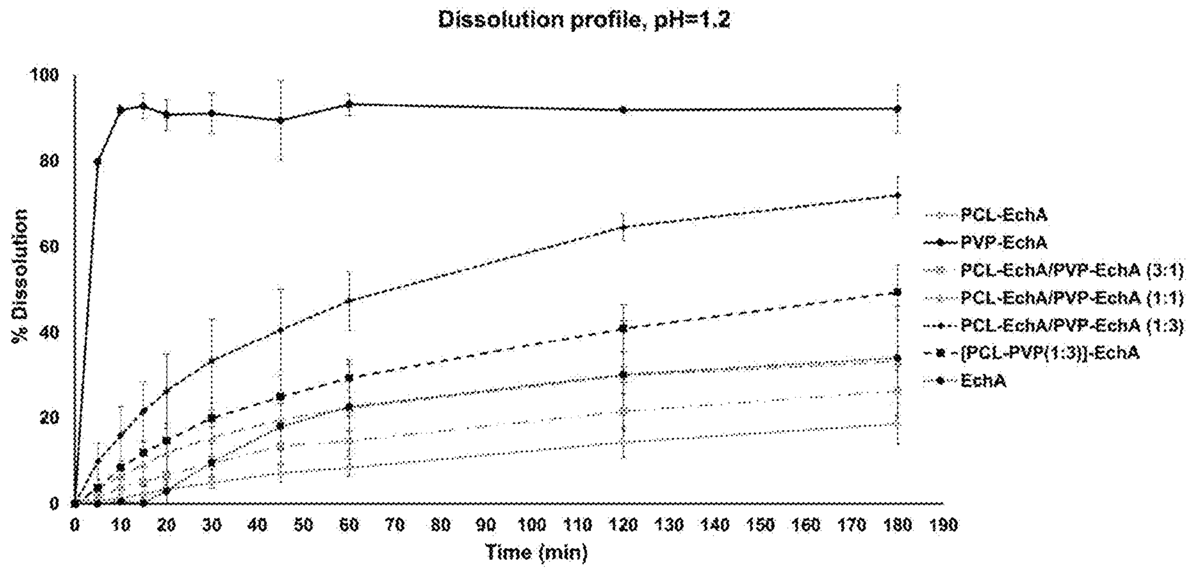
FIG. 3. Dissolution/release profiles of EchA and PCL-EchA, PVP-EchA, PCL-EchA/PVP-EchA (1:3), PCL-EchA/PVP-EchA (1:1), PCL-EchA/PVP-EchA (3:1) and [PCL-PVP(1:3)]-EchA fibrous matrices, at pH 1.2, 4.5 and, 6.8 (mean±SD, n=3).
Figure 3B:
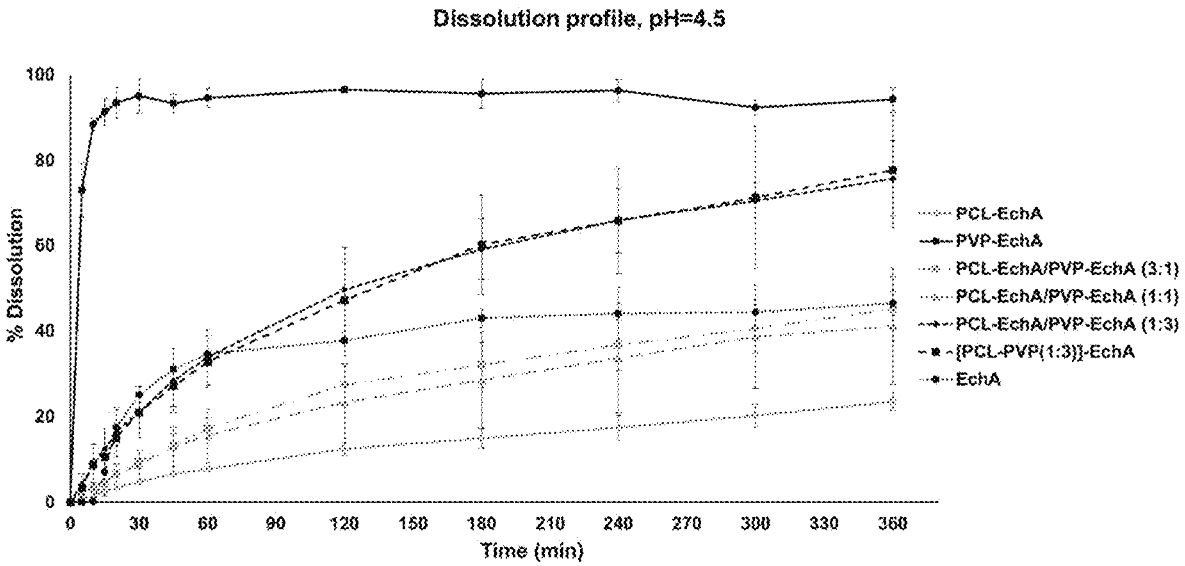
Figure 3C:
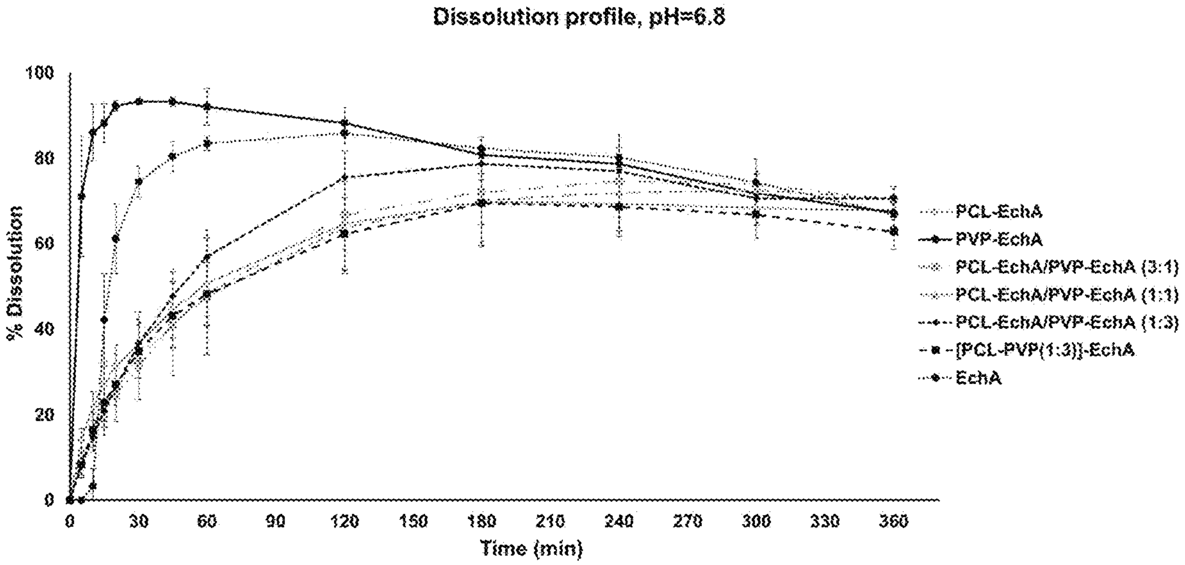

Dissolution tests for the prepared micro-/nanofibers and pure echinochrome A were performed in three different media, using the Vankel 750D dissolution apparatus with paddle method. The experiments were carried out in a total buffer volume of 500 mL at 37° C. and 50 rpm. The fibers were introduced in capsule sinkers, while cellulose capsules were employed for pure echinochrome A to avoid floating of the material during the experiment. Specifically, 20 mg fibers (containing 2 mg of echinochrome A) were dispersed in 500 mL of HCl 0.1 M, citric buffer 0.1M and phosphate buffer 0.1M, at pH 1.2, 4.5 and 6.8, respectively. At defined time intervals (5, 10, 15, 20, 30, 45, 60, 120, and 180 min for the dissolution study at pH 1.2 and 5, 10, 15, 20, 30, 45, 60, 120, 180, 240, 300, and 360 min for the dissolution studies at pH 4.5 and 6.8) a 3 mL sample was withdrawn from the dissolution medium of each flask and replaced with equal volume of fresh dissolution medium. The withdrawn samples were filtered via regenerated cellulose filters (Whatman, Spartan syringe filters, 0.45 μm), using 1 mL for the filters' saturation. The filtered volume was transferred in a UV transparent-corning 96 well flat clear plate and the UV absorbance of echinochrome A at 470 nm was measured using an Infinite M200 PRO TECAN plate reader. The dissolution studies (FIG. 3) revealed that the combination of two polymers, one with high hydrophilicity and one highly lipophilic, led to the development of micro-/nanofibers exhibiting variable release profiles of echinochrome A. For example, at pH 1.2 it is evident that within 60 min approx. 45% of echinochrome A has been released from the PCL-EchA/PVP-EchA (1:3) micro-/nanofibers, whereas only approx. 10% of echinochrome A has been released from the PCL-EchA/PVP-EchA (3:1) micro-/nanofibers.

The stability of the echinochrome A-containing micro-/nanofibers was evaluated according to the following protocol. 100 mg of polymeric micro-/nanofibers with echinochrome A were placed in 10 mL of acidified ethyl acetate. After 2 h the extract was filtered and the filtrate was evaporated to dryness under reduced pressure. The dry residue was dissolved in 10 mL of acidified ethanol. 300 μL of the solution were transferred to a quartz cuvette containing 2.7 mL ethanol and the absorbance at 470 nm was measured. The content of echinochrome A was calculated from a calibration curve. Measurements were performed at 1, 3, 6, 9, 12 and 24 months after preparation of the micro-/nanofibers. It was established that echinochrome A remains stable in the polymeric micro-/nanofibrous matrices for at least two years, which is much longer than in known pharmaceutical forms (60 h). As evidenced, the incorporation of echinochrome A in polymeric micro-/nanofibers greatly prolongs the stability of echinochrome A.

REFERENCES

1. Anderson et al. Comp. Biochem. Physiol., 1969, 28, 333-345
2. Mishchenko et al. Pharm. Chem. J., 2003, 37, 48-52
3. Elyakov et al. European Patent 1,121,930, 14 Nov. 2007
4. U.S. Pat. No. 6,410,601B2 (Tikhookeansky Institut Bioorganicheskoi Khimii Dalnevostochnogo Otdeleniya Rossiiskoi Akademii Nauk), 25 Jun. 2002; EP1121929B1 (Tikhookeansky Institut Bioorganicheskoi Khimii Dalnevostochnogo Otdeleniya Rossiiskoi Akademii Nauk), 8 Aug. 2001
5. Artyukov et al. J. Clin. Med., 2020, 9, 1494; Lennikov et al. Mol. Vis., 2014, 20, 171-177; Oh et al. Mar. Drugs, 2019, 17, 622; Seol et al. Mar. Drugs, 2021, 19, 550
6. Fedoreyev et al. Mar. Drugs, 2018, 16, 509
7. Sadek et al. J. Food Biochem., 2022, 46, e13729
8. Kim et al. Mar. Drugs., 2021, 19, 412
9. RU 2500396 C2, (Zakrytoe aktsionemoe obshchestvo "Tsentr novykh tekhnologij i biznesa", Uchrezhdenie Rossijskoj akademii nauk Tikhookeanskij institut bioorganicheskoj khimii Dal'nevostochnogo otdelenija Rossijskoj akademii nauk) 10 Dec. 2013
10. RU 2530886 C1, (Gosudarstvennoe bjudzhetnoe uchrezhdenie "Ufimskij nauchno-issledovatel'skij institute glaznykh boleznej Akademii nauk Respubliki Bashkortostan", Federal'noe gosudarstvennoe bjudzhetnoe uchrezhdenie nauki Tikhookeanskij institute bioorganicheskoj khimii im. G.B. Eljakova Dal'nevostochnogo otdelenija Rossijskoj akademii nauk) 20 Oct. 2014; Bikbov et al. Pharm. Chem. J. 2018, 51, 980-984
11. Yermak et al. Carbohydr. Polym., 2021, 272, 118479
12. Yermak et al. Mar. Drugs, 2017, 15, 337
13. Yermak et al. Mar. Drugs, 2018, 16, 324
14. RU 2684783 C1, (Federalnoe gosudarstvennoe byudzhetnoe uchrezhdenie nauki Tikhookeanskij institut bioorganicheskoj khimii im. G. B. Elyakova Dalnevostochnogo otdeleniya Rossijskoj akademii nauk (TIBOKH DVO RAN)) 15 Apr. 2019; RU 2697886 C1, (Federalnoe gosudarstvennoe byudzhetnoe uchrezhdenie nauki Tikhookeanskij institut bioorganicheskoj khimii im. G. B. Elyakova Dalnevostochnogo otdeleniya Rossijskoj akademii nauk (TIBOKH DVO RAN), Federalnoe gosudarstvennoe byudzhetnoe nauchnoe uchrezhdenie "Nauchno-issledovatelskij institut epidemiologii i mikrobiologii im. G.P. Somova" (FGBNU "Nil EM imeni G.P. Somova")) 21 Aug. 2019: RU 2697887 C1, (Federalnoe gosudarstvennoe byudzhetnoe uchrezhdenie nauki Tikhookeanskij institut bioorganicheskoj khimii im. G. B. Elyakova Dalnevostochnogo otdeleniya Rossijskoj akademii nauk (TIBOKH DVO RAN), Federalnoe gosudarstvennoe byudzhetnoe nauchnoe uchrezhdenie "Nauchno-issiedovatelskij institut epidemiologii i mikrobiologii im. G.P. Somova" (FGBNU "Nil EM imeni G.P. Somova")) 21 Aug. 2019
15. Vasileva et al. Vestnik FEB RAS, 2018, No 6 Supplement, 169-170
16. RU 2651042 C1, (Federalnoe gosudarstvennoe byudzhetnoe uchrezhdenie nauki Tikhookeanskij institut bioorganicheskoj khimii im. G. B. Elyakova Dalnevostochnogo otdeleniya Rossijskoj akademii nauk (TIBOKH DVO RAN)) 18 Apr. 2018

The invention claimed is:

1. A pharmaceutical composition for use as a medicament, comprising two or more biocompatible polymers or one or more diblock copolymer and echinochrome A characterized in that echinochrome A is incorporated in micro-/nanofibers of the biocompatible polymers or the diblock copolymer and that the said biocompatible polymers or the blocks of the said copolymer have different hydrophilicity and pH sensitivity so that the pharmaceutical composition provides controlled release and/or targeted delivery of echinochrome A in different pH environments.

2. A pharmaceutical composition for use as a medicament according to claim 1, wherein the biocompatible polymers are natural and/or synthetic.

3. A pharmaceutical composition for use as a medicament according to claim 1, wherein the micro-/nanofibers are fabricated through electrospinning or centrifugal spinning or meltblowing or self-assembly or phase separation and extrusion of echinochrome A dissolved or dispersed in the said biocompatible polymers.

4. A pharmaceutical composition for use as a medicament according to claim 1, wherein the micro-/nanofibers are fabricated through electrospinning of a solution of echinochrome A dissolved or dispersed in the said biocompatible polymers in a concentration between 1 and 50% w/w.

5. A pharmaceutical composition for use as a medicament according to claim 1, wherein the said biocompatible polymers are blended in one spinning solution that is electrospun as is or are used to form independent spinning solutions that are simultaneously electrospun using a parallel or antiparallel setup to fabricate a composite non-woven.

6. A pharmaceutical composition according to claim 1 for use in the treatment of inflammatory diseases.

7. A pharmaceutical composition for use as a medicament according to claim 1 characterized in that the said composition is administered by oral or transdermal or buccal or nasal administration or a combination thereof.

8. A pharmaceutical composition for use as a medicament according to claim 2, wherein the natural polymers are selected from the group consisting of alginate, chitosan, gelatin, hyaluronic acid, silk fibroin, glycosaminoglycans, ulvan, carrageenan, fucoidan, and combinations thereof.

9. A pharmaceutical composition for use as a medicament according to claim 2, wherein the synthetic polymers are selected from the group consisting of polyvinylpyrrolidone, polycaprolactone, polyethylene oxide, cellulose acetate, methyoxypropyl cellulose, polylactic acid, polyhydroxybutyrate, polyglycolic acid, polyethylene glycol, polyacrylic acid, polyurethane, and combinations thereof.

* * * * *